United States Patent [19]

Broyles

[11] 4,390,599
[45] Jun. 28, 1983

[54] ENHANCED RECOVERY MEMORY METAL DEVICE

[75] Inventor: Harry C. Broyles, Sunnyvale, Calif.

[73] Assignee: Raychem Corporation, Calif.

[21] Appl. No.: 173,948

[22] Filed: Jul. 31, 1980

[51] Int. Cl.³ .............................................. C22F 1/00
[52] U.S. Cl. ................................... 428/597; 428/596; 428/913
[58] Field of Search ..................... 428/597, 596, 913; 52/672, 675, 670, 671; 29/6.1, 6.2, 447; 228/127; 285/114; 411/909

[56] References Cited

U.S. PATENT DOCUMENTS

| | | | |
|---|---|---|---|
| 1,055,675 | 3/1913 | Smith | 29/6.2 |
| 2,018,085 | 10/1935 | Otte | 52/671 |
| 3,206,536 | 9/1965 | Goodloe | 52/670 |
| 3,280,446 | 10/1966 | Borello | 29/6.2 |
| 3,312,538 | 4/1967 | Hansson | 428/596 |
| 3,513,429 | 5/1970 | Helsop | 29/447 |
| 3,546,075 | 12/1970 | Sheetz | 428/596 |
| 3,591,351 | 7/1971 | Ullman | 428/597 |
| 3,913,444 | 10/1975 | Otte | 29/447 |
| 4,035,007 | 7/1977 | Harrison et al. | |
| 4,198,081 | 4/1980 | Harrison | 29/447 |
| 4,237,609 | 12/1980 | Clabburn | 428/913 |

FOREIGN PATENT DOCUMENTS 537553  6/1941  United Kingdom .................. 52/670

OTHER PUBLICATIONS

"A Summary of Recent Research on the Nitinol* Alloys . . . ", Buehler et al., Pergamon Press, NY (1968), pp. 105-120.
"Shape Memory Effect . . . in 304 Type Stainless Steel", Enami et al., Scripta Metallurgica, vol. 5, Pergamon Press, Inc. (1971), pp. 663-667.
Metals Handbook, American Society for Metals, Cleveland, Ohio (1936), pp. 336-J.
Republic Enduro Stainless Steels, Republic Steel Corporation, Cleveland, Ohio, (1951), pp. 63, 65, 67-68.

Primary Examiner—L. Dewayne Rutledge
Assistant Examiner—J. J. Zimmerman
Attorney, Agent, or Firm—James W. Peterson

[57] ABSTRACT

The invention is a device utilizing a sheet of memory metal being recoverable in substantially a single direction within the plane of said sheet of memory metal wherein said sheet has a plurality of perforations of a particular pattern and shape which enhance the recovery of said sheet in said direction beyond the inherent recovery of the memory metal comprising said sheet.

15 Claims, 4 Drawing Figures

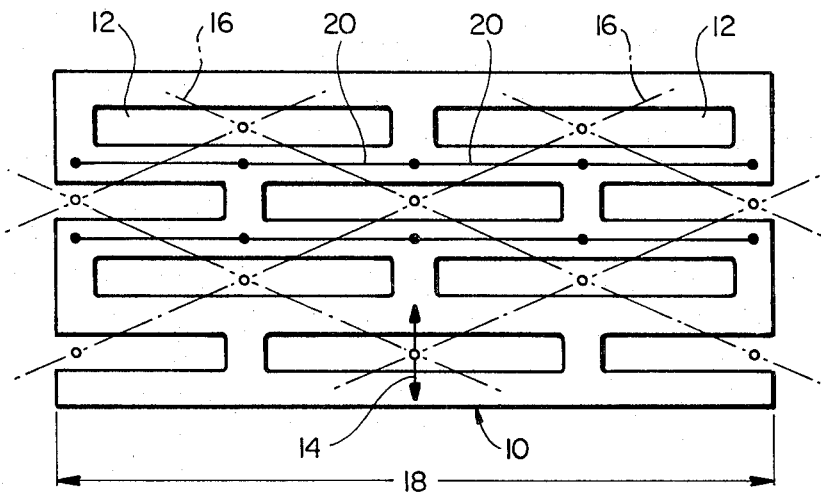
FIG_1
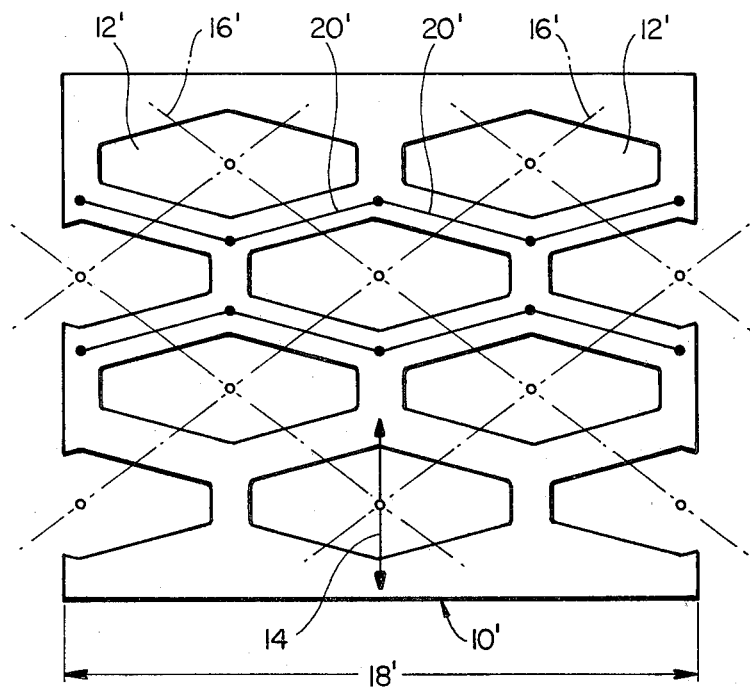
FIG_2

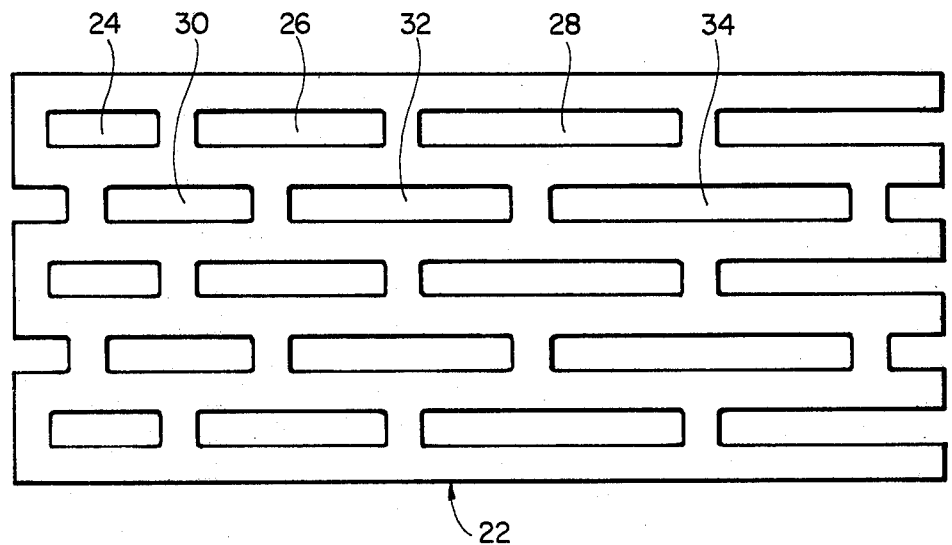
FIG_3
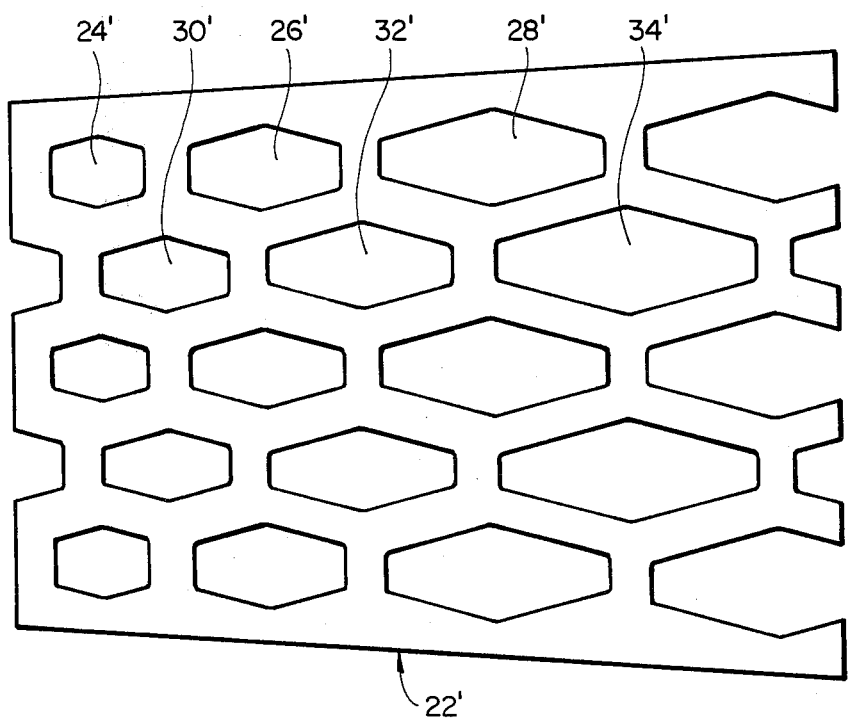
FIG_4

ENHANCED RECOVERY MEMORY METAL DEVICE

BACKGROUND OF THE INVENTION

The instant invention is a device which enhances the recovery of a sheet of memory metal beyond the inherent recovery of the memory metal comprising said sheet. Memory metals are alloys which manifest the shape—memory effect—such alloys are well known and they, and the shape—memory effect, are discussed in e.g., "Shape—Memory Alloys", Scientific American, v. 281, pp 74/82 (November 1979). In the past such memory metals have been utilized in mechanical composite pipe couplings to force tensile load-bearing members into gripping contact with pipes and tubing. Commonly assigned Australian Pat. No. 74153/74 to C. L. Martin discloses the use of such memory metals as drivers to be utilized externally and internally with respect to pipes. The recovery capability of the memory metal in such cases is limited to the inherent recovery of the memory metal comprising said drivers, which is in the range of 4-9% maximum for solid metal members. Commonly assigned British Pat. No. 1,554,431 to C. L. Martin discloses the use of various configurations of memory metal alloy to secure patch members over ruptured pipe sections. Martin discloses the use of a helical spring-like memory metal driver to achieve a higher degree of recovery in the radial direction. Likewise, commonly assigned U.S. Pat. No. 4,197,880 to J. M. Cordia discloses a compressed, axially slit, cylindrical memory metal driver member which is held is a radially compressed configuration by a thermoplastic retainer means, and is used to drive a foamable material toward the inside wall of a pipe. The driver disclosed by Cordia is axially slit to enhance its radial recovery. Neither of the Martin patents nor the Cordia patent suggest the construction of a highly articulated and therefore recoverable device comprising a sheet of memory metal having a plurality of perforations of related shape and pattern which will enhance the recovery beyond the inherent recovery of the memory metal comprising said sheet. Further, none of the above described references suggest a sheet which can be configured into a continuous geometric configuration, for example, a cylindrical shape having a continuous circumference necessary for the application of truly uniform pressure. Further, because of the continuous circumference the cylindrical embodiment of the instant invention exerts greater pressure that the above described references. It should be apparent that the unique sheet of the instant invention is useful in a variety of geometric configurations of said sheet ranging from flat to, for example, cylindrical configurations, none of which are suggested in the above described references.

It is a primary object of the instant invention to provide a sheet of memory metal having enhanced recoverability beyond the inherent recovery of the memory metal comprising said sheet.

It is another object of the instant invention to provide a sheet of memory metal which is recoverable in substantially a single direction within the plane of said sheet.

It is yet another object of the instant invention to provide a sheet of memory metal which recoverable in more than one direction within the plane of said sheet.

SUMMARY OF THE INVENTION

The purpose of the instant invention is to provide a sheet of memory metal which is recoverable in substantially a single direction within the plane of said sheet.

To accomplish this purpose, the instant invention provides a sheet having a plurality of perforations of particular shape and arranged in a particular pattern, said shape and pattern enhancing the recovery of said sheet in said direction beyond the inherent recovery capabilities of the memory metal itself.

The term "inherent recovery" as used herein, refers to the extent of recovery available when a memory metal article, which has been deformed in simple tension or compression while in a martensitic state, returns to the austenitic state in the absence of restraining forces. Although this inherent recovery is theoretically high for single crystals, in practice the inherent recovery of a polycrystalline memory metal is about 4% to about 9%.

DESCRIPTION OF THE DRAWING

FIG. 1 illustrates in plan view the device of the instant invention in a first geometric state.

FIG. 2 illustrates in plan view the device shown in FIG. 1 in a second geometric state.

FIG. 3 illustrates in plan view an alternate embodiment of the device shown in FIG. 1 in a first geometric state.

FIG. 4 illustrates in plan view the device of FIG. 3 in a second geometric state.

DESCRIPTION OF THE PREFERRED EMBODIMENT

With continued reference to the drawing, FIG. 1 illustrates sheet 10 of the instant invention having perforations 12 contained therein. Sheet 10 is made from a memory metal, that is an, alloy which manifests the shape—memory effect. Especially suitable alloys for sheet 10 are made from a ternary or quaternary alloy of copper, zinc, aluminum and/or manganese or from a nickel-titanium binary or ternary alloy. The plurality of perforation s 12 are of a particular shape and are arranged in a particular pattern, said shape and pattern enhancing the recovery of said sheet in substantially a single direction noted at 14 within the plane of said sheet 10. FIG. 2 illustrates said recovery substantially in direction 14. FIG. 1 illustrates a first geometric state of sheet 10 wherein sheet 10 is in a compressed or non-expanded condition. FIG. 2 illustrates a second geometric state for sheet 10' and perforations 12' when sheet 10' and perforations 12' are in their recovered or expanded condition relative to FIG. 1. In operation, FIG. 1 would represent the first geometric state of sheet 10 before application of heat and FIG. 2 would represent the second geometric state of sheet 10' and perforations 12' after application of heat. In this regard, FIG. 1 represents sheet 10 as a compressed member which expands upon heating. It is within the scope of the invention to reverse the effect of heating, whereby FIG. 2 would represent a sheet 10' and perforations 12' before heating, said sheet 10' and perforation 12' being in an expanded condition which upon heating will recover to the first geometric shape shown in FIG. 1 wherein sheet 10 is non-expanded.

It can be seen in FIG. 1 that perforations 12 are of a particular range that is generally rectangular and that perforations 12 are arranged in a particular pattern that is in the form of a rhombic lattice. The rhombic lattice is clearly shown by the use of center lines 16 which interconnect the geometric centers of the perforations 12. This rhombic lattice clearly allows expansion or contraction in direction 14 which constitutes a diagonal of said lattice. It can be seen in FIG. 2 that the center lines 16' of perforations 12' likewise define a rhombic lattice, the direction of recovery 14' again being a diagonal of said lattice.

FIG. 1 illustrates perforations 12 to be generally rectangular in shape and being relatively narrow in width corresponding to direction 14. This construction enables recovery to a substantially flat diamond shape of perforation 12' in FIG. 2. The interrelationship between perforations 12 in FIG. 1 and perforations 12' in FIG. 2 allows substantial recovery in direction 14 within the plane of said sheet 10. It can be seen that the initial length 18 of sheet 10 in FIG. 1 is decreased to a shorter length 18' in FIG. 2 upon recovery of sheet 10. It should be apparent that there is a geometric relationship between the width/length of perforations 12 and the amount of dimensional change 18 to 18'. It should likewise be apparent that a change in the ratio of width/length of perforation 12 will change the amount of recovery and therefore the difference between 18 and 18'. It is within the scope of the invention to vary this ratio to create sheets which are capable of enhanced motion in more than one direction within the plane of said sheet, i.e., expansion in one direction and contraction in the perpendicular direction.

FIGS. 1 and 2 can likewise be viewed as illustrating two dimensional arrays of co-acting lever arms within the plane of a sheet. These co-acting arms 20 in FIG. 1 are shown as center line segments of sheet 10. It can be clearly seen that the co-acting arms 20 of FIG. 1 are bent into the co-acting arms 20' of FIG. 2.

FIG. 3 illustrates sheet 22 having varied perforations 24, 26 and 28; perforation 26 being longer than perforation 24 and perforation 28 being longer than perforation 26. The similar increasing width relationship exists with regard to perforations 30, 32 and 34. The embodiment of FIG. 3 therefore represents a sheet having a plurality of perforations, said perforations being varied in shape but being arranged in a particular pattern.

FIG. 4 illustrates the device of FIG. 3 in a recovered or expanded condition. It can be seen that the varied shapes 24, 26, 28, 30, 32 and 34 in their particular pattern recover to similar diamond shapes 24', 26', 28' 30', 32' and 34' in FIG. 4. The geometric interrelationship between FIG. 3 and FIG. 4 provides a sheet which is recoverable to a varying extent substantially in one direction within the plane of said sheet, i.e. to go from a generally rectangular configuration to a generally fan shaped configuration.

FIGS. 1 through 4 provide structure for amplifying the available recovery motion of a memory metal. The particular pattern illustrated in FIG. 2 may be compressed or reduced by as much as 25% to 75% in direction 14. Stated another way, the pattern illustrated in FIG. 1 allows for a memory metal structure to expand some 50 to 300% in direction 14. The sheet illustrated in FIGS. 1 and 2 may be formed into a generally cylindrical configuration. A use for such a configuration is diclosed in the commonly assigned and contemporaneously filed application of Cook et al. U.S. Pat. No. 4,355,644, the disclosure of which is incorporated herein by reference.

It is likewise within the scope of the invention to form the sheets illustrated in FIGS. 1 through 4 into generally conical configurations or, for that matter, almost any three-dimensional geometric configuration to take advantage of the one-or two-dimensional recovery of said sheets within their planes.

The sheets illustrated in FIGS. 1 through 4, and the various configurations that can be made from said sheets by one skilled in the art, allow utilization of the recovery of said configurations as drivers in the Martin and Cordia patents and as the delivery means discussed in the application of Cook et al.

The amount of recoverable motion available is primarily a function of perforation slot width, length spacing and the amount of bending strain per lever arm. These variables can be balanced in various combinations to yield similar or identical performance. Likewise, the shape of the perforations will vary in compressed or non-expanded condition from substantially rectangular to oval. The corners of a rectangular shape or radius help to accomodate bending stress concentrations. It is understood that perforations may be machined, etched, stamped, or otherwise formed.

Although the present invention has been described in considerable detail with reference to certain preferred versions thereof, other versions are possible. Therefore, the spirit and scope of the appended claims should not necessarily be limited to the description of the preferred versions contained herein.

What is claimed is:

1. A device comprising a sheet of memory metal, said metal possessing a thermoelastic transition between a martensitic state and an austenitic state, said sheet being deformed dimensionally while in its martensitic state and capable of recovering to its non-deformed dimension in its austenitic state in substantially a single direction within the plane of said sheet, said sheet having a plurality of perforations, said perforations being in a particular shape and being arranged in a particular pattern, said shape and pattern enhancing the recovery of said sheet to deliver motion and force in said direction beyond the inherent recovery of the memory metal comprising said sheet if said perforations were not present.

2. A device as in claim 1 wherein the pattern of said perforations is a rhombic lattice and the direction of recovery of said sheet is one of the diagonals of said lattice.

3. A device as in claim 1 wherein said perforations create a two-dimensional array of co-acting lever arms within the plane of said sheet, the enhanced recovery of said sheet being provided by the bending of said lever arms within the plane of said sheet.

4. A device as in claim 1 wherein said sheet is substantially flat.

5. A device as in claim 1 wherein said sheet defines a cylindrical surface.

6. A device as in claim 1 wherein said sheet defines a generally conical surface.

7. A device as in claim 5 or 6 wherein the recovery of said device is generally radial.

8. A device as in claim 5 or 6 wherein the recovery of said device is generally axial.

9. A device as in claim 1 wherein the shape of said perforations comprise an elongated rectangle.

10. A device as in claim 1, wherein the inherent recovery of the metal comprising said sheet is at least 4%.

11. A device as in claim 1 wherein the metal comprising said sheet is an alloy comprising nickel and titanium.

12. A device as in claim 1 wherein the metal comprising said sheet is an alloy of copper and zinc.

13. A device comprising a sheet of memory metal, said metal possessing possessing a thermoelastic transition between a martensitic state and an austenitic state, said sheet being deformed dimensionally while in its martensitic state and capable of recovering to its non-deformed dimension in its austenitic state to a varying extent substantially in one direction within the plane of said sheet, said sheet having a plurality of perforations, said perforations being varied in shape and being arranged in a particular pattern, said varied shapes and said pattern enhancing the recovery of said sheet to deliver motion and force in said direction beyond the inherent recovery of the memory metal comprising said sheet if said perforations were not present.

14. A device comprising a sheet of memory metal, said metal possessing a thermoelastic transition between a martensitic state and an austenitic state, said sheet being deformed dimensionally while in its martensitic state and capable of recovering to its non-deformed dimension in its austenitic state such that substantial motion is realized in two directions within the plane of said sheet, said sheet having a plurality of perforations, said perforations being of a particular shape and being arranged in a particular pattern, said shapes and said pattern enhancing recovery of said sheet to deliver motion and force in said directions beyond the inherent recovery of the memory metal comprising said sheet if said perforations were not present.

15. A device as in claim 11 wherein the shape of said perforations comprise a square.

* * * * *

UNITED STATES PATENT AND TRADEMARK OFFICE
CERTIFICATE OF CORRECTION

PATENT NO. : 4,390,599

DATED : June 28, 1983

INVENTOR(S) : Harry C. Broyles

It is certified that error appears in the above-identified patent and that said Letters Patent are hereby corrected as shown below:

Column 2, line 67, delete "range" and insert --shape--.

Signed and Sealed this

Tenth Day of April 1984

[SEAL]

Attest:

GERALD J. MOSSINGHOFF

Attesting Officer

Commissioner of Patents and Trademarks